United States Patent [19]
Dagher

[11] Patent Number: 4,945,574
[45] Date of Patent: Aug. 7, 1990

[54] PROTECTIVE MASK

[75] Inventor: F. Joseph Dagher, St. Petersburg, Fla.

[73] Assignee: DHL Research and Development Corporation, Philadelphia, Pa.

[21] Appl. No.: 318,048

[22] Filed: Mar. 2, 1989

Related U.S. Application Data

[63] Continuation-in-part of Ser. No. 153,858, Feb. 9, 1988, abandoned.

[51] Int. Cl.⁵ .............................................. A61F 9/04
[52] U.S. Cl. .............................................. 2/9; 2/206; 128/863
[58] Field of Search .................. 2/206, 9, 10, 427, 431, 2/12; 128/863

[56] References Cited

U.S. PATENT DOCUMENTS

| | | | |
|---|---|---|---|
| 1,475,105 | 11/1923 | Aasen | 128/863 |
| 2,342,982 | 2/1944 | Stern et al. | 2/9 |
| 3,038,470 | 6/1962 | Campbell | 2/9 X |
| 3,041,624 | 7/1962 | Cutrona, Jr. | 2/206 X |
| 3,991,753 | 11/1976 | Viesca | 2/9 X |
| 4,583,535 | 4/1986 | Saffo | 2/206 X |
| 4,701,965 | 10/1987 | Landis | 2/9 X |

FOREIGN PATENT DOCUMENTS

| | | | |
|---|---|---|---|
| 0015181 | 2/1956 | Fed. Rep. of Germany | 2/9 |
| 0074138 | 2/1928 | Sweden | 2/206 |
| 0242310 | 12/1925 | United Kingdom | 2/10 |

Primary Examiner—Peter Nerbun
Attorney, Agent, or Firm—Caesar, Rivise, Bernstein, Cohen & Pokotilow, Ltd.

[57] ABSTRACT

A protective mask comprising an imperforate, transparent shield mounted on the brow and extending over the face of a person wearing the mask. The shield includes an anteriorly protruding portion spaced sufficiently away from the wearer's face to enable spectacles or other optical devices to be worn by the user. The anteriorly protruding portion includes an outwardly flaring upper portion and a downwardly flaring lower portion, with the junction between the upper and lower portions being a non-sharp, gradually curved section which minimizes the amount of visual distortion experienced by the user. Attached in a longitudinal fashion, adjacent each side edge of the shield, is a malleable, form-adjusting strip, the bending of which foreshortens the shield, causing it to bow-out anteriorly to accommodate the use of a variety of sized eyegear to be worn with the mask.

8 Claims, 3 Drawing Sheets

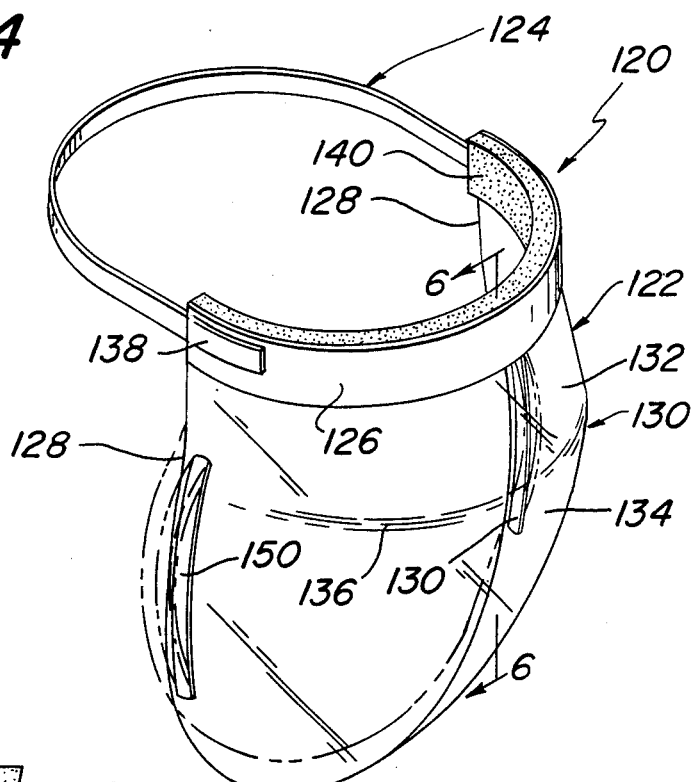
FIG. 4
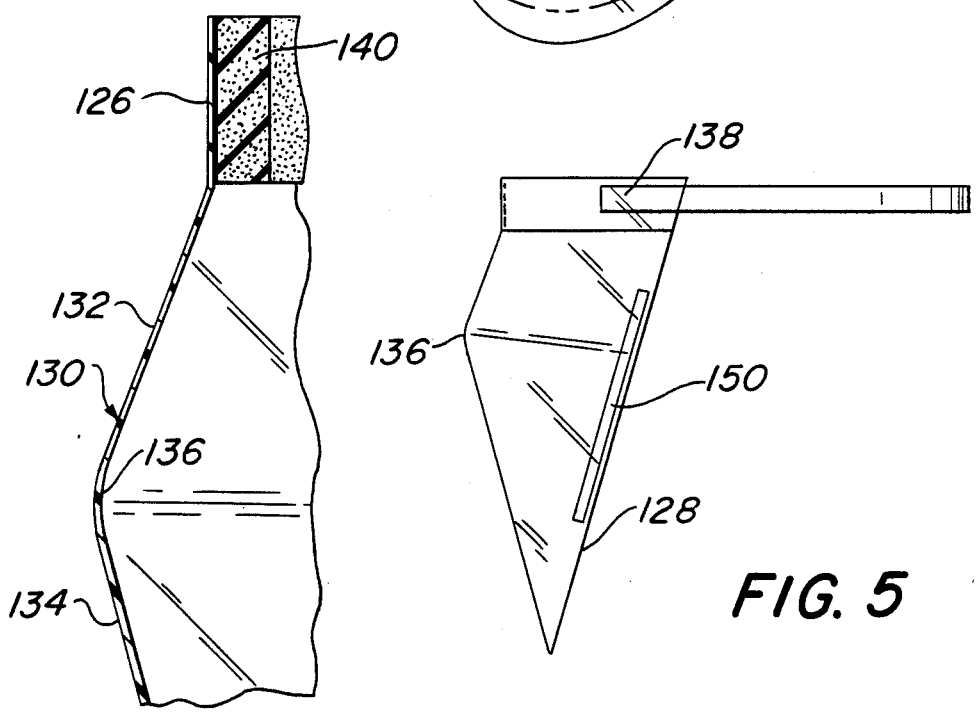
FIG. 6
FIG. 5

PROTECTIVE MASK

RELATED APPLICATION

This application is a continuation-in-part of copending application Ser. No. 07/153,858 filed Feb. 9, 1988, now abandoned.

BACKGROUND OF THE INVENTION

This invention relates generally to medical and surgical devices and more particularly to masks to be worn by medical/surgical/dental personnel.

In this age when fatal diseases, such as AIDS, which are transmitted by contamination with blood or other body fluids, has reached epidemic proportions, protection against accidental contamination with such fluids is of critical importance to those persons who, due to their vocation, are at a high risk. Thus, health care providers, such as surgeons, anesthesiologists, surgical residents, medical students, nurses, dentists, dental hygienists and assistants, etc., are at a very high risk of contracting AIDS or other fluid-borne viruses when operating on or managing patients carrying such disease, e.g., AIDS patients or patients with a positive HIV serum.

Heretofore, health care providers have taken various precautions to prevent contamination by the use of gloves and/or masks. The masks which have been typically utilized heretofore are conventional fabric or paper masks which cover the nose and mouth. Such masks leave the eyes uncovered so as not to impede visibility. In order to protect the eyes, it is also a common practice for various health care providers to wear glasses, spectacles or some other eye shield means.

Other types of facial masks for use in a wide variety of situations, are disclosed in the prior art. Prior patents disclosing such facial masks include Aasen, U.S. Pat. No. 1,475,105; Stern et al, U.S. Pat. No. 2,342,982; Campbell, U.S. Pat. No. 3,038,470; Cutrona, Jr., U.S. Pat. No. 3,041,624; Viesca, U.S. Pat. No. 3,991,753; Saffo, U. S. Pat. No. 4,583,535; Landis, U.S. Pat. No. 4,701,965; Romer, German Pat. No. 15181; and Eliat, U.K. Pat. No. 242310. The masks disclosed in the aforementioned prior patents are believed to be deficient in a number of respects, including the ability to be conformed or shaped to accommodate different facial configurations and/or the use of eyewear in various sizes and shapes.

The Stern et al. '105 patent describes a transparent, adjustable facial shield to be used for protection against industrial plant hazards. Although the leather headstrap provides for adjustability, the necessary adjustment is believed to be awkward and time consuming. Further, the device is lacking in any means to adjust the contour thereof to accommodate different facial configurations and/or the use of eyewear in a variety of sizes and shapes, worn by the users of the device.

The Eliat '310 British patent and the Romer '181 German patent disclose facial masks which are designed to sit a distance from the user's eyes. However, neither of these latter patents are believed to provide a structure which fits comfortably on users wearing eyewear of various sizes and shapes. In the Eliat construction a stiffening material, such as wire, is employed to maintain the arcuate shape of the transparent facial shield. There is no disclosure that the stiffening material is intended for, or capable of, use in varying the shape or contour of the mask.

The Cutrona '624 patent discloses a hand-held facial spray shield containing a malleable retaining strip secured in a transverse fashion on the shield face.

Notwithstanding the foregoing, a need presently exists for a face mask which not only allows unimpeded visibility, but which also protects the whole face, including the eyes, conjunctiva, etc., and which can be worn during medical/surgical/ dental procedures being carried out, while not adversely affecting the ability of the health care providers to carry out the desired procedures.

OBJECTS OF THE INVENTION

Accordingly it is the general object of the instant invention to provide a face mask which overcomes the disadvantages of the prior art.

It is a further object of this invention to provide a face mask which protects the whole face, including the eyes, conjunctiva, etc.

It is still a further object of this invention to provide a face mask which is simple in construction and low in cost.

It is still a further object of this invention to provide a face mask which is readily disposable.

It is yet a further object of this invention to provide a face mask which can be worn with conventional cloth or paper face masks and/or head coverings or hoods.

It is still a further object of this invention to provide a face mask which is capable of being readily shaped to the wearer's facial contours and to the wearer's use of eyewear of a variety of sizes and shapes.

SUMMARY OF THE INVENTION

These and other objects of the instant invention are achieved by providing a protective mask for use by medical and/or dental personnel comprising a mounting means for securing the mask to the head of a person in conformity with the person's brow. An imperforate shield which is formed of a transparent material and of a sufficient width and height to cover substantially the entire face of the wearer is attached to the mounting means and includes an anteriorly protruding portion extending downwardly from the mounting means to cover the wearer's face. The anteriorly protruding portion of the shield includes an outwardly flaring upward portion and a downwardly flaring lower portion. The junction between these upper and lower portions is a non-sharp, curved portion for minimizing the amount of visual distortion experienced by the user, as compared to forming this junction by a sharp bend or fold.

In a preferred embodiment of the invention, form adjusting strips are mounted vertically adjacent side edges of the mask, most preferably bridging the upper and lower shield portions thereof. These form adjusting strips enable the user to adjust the mask to conform to the individual's facial contours. Moreover, the vertically oriented adjusting strips permit foreshorting of the mask, to thereby cause the mask to bow-out anteriorally to accommodate eyewear of various sizes and shapes.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 4 is a perspective view of an alternative and preferred embodiment of the protective mask of the subject invention;

FIG. 5 is a side elevational view of the protective mask shown in FIG. 4; and

FIG. 6 is an enlarged sectional view taken along line 6—6 of FIG. 4.

DETAILED DESCRIPTION OF THE PREFERRED EMBODIMENT

Figure 1:
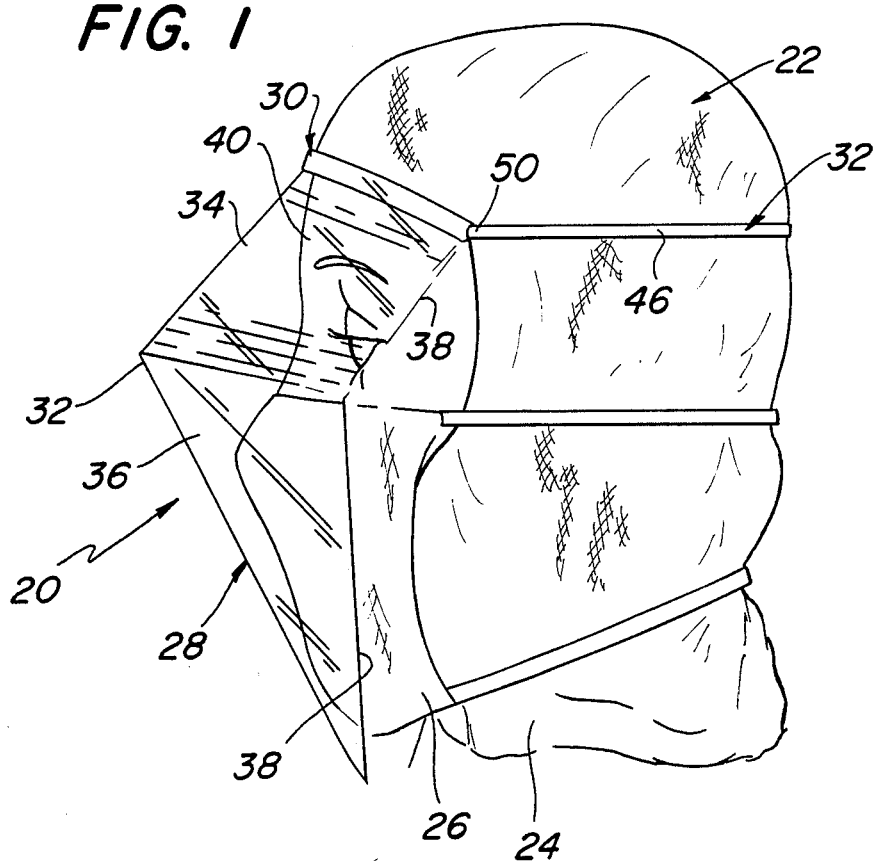
FIG. 1 is a side elevational view of the protective mask of the subject invention shown in use in a typical application by medical/surgical/dental personnel.
Figure 3:
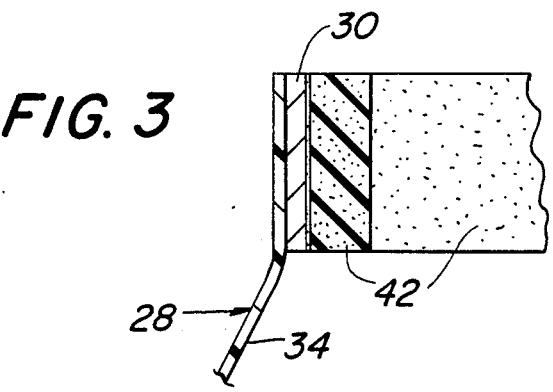
FIG. 3 is an enlarged sectional view taken along line 3—3 of FIG. 2.

Referring now to the various figures of the drawings wherein like reference characters refer to like parts, there is shown at 20 in FIG. 1, a protective mask or shield constructed in accordance with the subject invention. The mask 20 is arranged to be worn on the head 22 of a person who may be exposed to contaminated fluids. In the embodiment shown herein, the mask 20 is shown worn on the head of a surgeon. Thus, as shown in FIG. 1, the surgeon, in addition to wearing the protective mask 20, is also shown wearing a conventional hood or cap 24 covering his/her head, the sides of his/her face and neck, and a conventional nose/mouth mask 26 covering his/her nose and mouth.

As can be seen clearly in FIG. 1, the subject mask 20 covers virtually the entire face of the wearer by extending from the brow down to slightly below the chin and across the full width of the face. The shield is transparent to allow the wearer unimpeded visibility while protecting his/her face, eyes, conjunctiva, etc., from contact with any contaminated fluid.

The mask 20 basically comprises transparent shield means 28, supporting frame means 30, and mounting means 31. The shield is formed of a transparent material, such as clear or tinted plastic, which is imperforate, to serve as an impenetrable barrier for any virus, bacteria or other contaminant. The mask is of a sufficient size to extend over substantially the entire face of virtually any person. Thus, it extends from the brow down to below the chin and across the full width of the face. Moreover, the shield 28 is shaped to form an anteriorly protruding portion 32. To that end, the shield includes an outwardly flaring upper portion 34 and an inwardly flaring lower portion 36. The projecting portion 32 is located so that it is disposed opposite the wearer's eyes yet spaced a sufficient distance from the face to permit the mask to be worn by persons having a variety of facial features, e.g., to enable any person to wear the mask comfortably, irrespective of the size of the person's nose. In fact, the projecting portion 32 is so configured to enable the person to wear spectacles or other optical devices under the mask.

Figure 2:
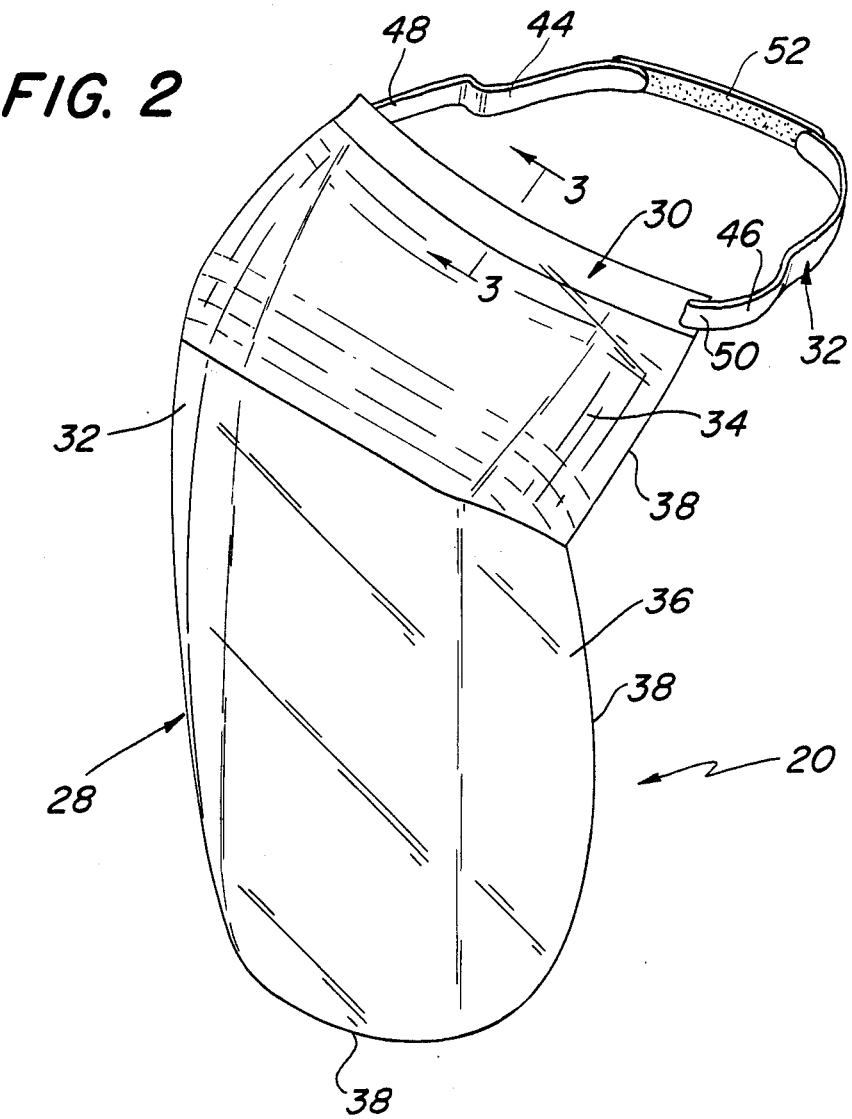
FIG. 2 is an enlarged perspective view of the protective mask shown in FIG. 1.

As can be seen clearly in FIG. 2, each of the sections 34 and 36 of the mask is slightly arcuate from side to side to generally conform to the curvature of a person's face. The marginal edges of the mask are denoted by the reference numeral 38 and may be either curved or straight, as desired.

The frame 30 is arranged to support the shield 28 from the brow 40 of the person. To that end, the frame 30 basically comprises an elongated strip of malleable material, such as aluminum, which is fixedly secured, such as through an adhesive (not shown) to the inside surface of the top marginal edge of the upper section 34 of the mask. The band 30 extends the entire width of the mask. Fixedly secured to the inner surface of the frame 30 is a strip of cushioning material 42, such as felt or foam rubber. The strip of cushioning material is secured to the frame by an adhesive (not shown) and extends the entire length of the frame. The cushioning strap serves to directly engage the brow to provide a comfortable surface against which the brow bears when the mask is in place. As will be appreciated by those skilled in the art, by virtue of the fact that the frame 30 is malleable or conformable, it can be bent to conform to the precise shape of the wearer's brow to thereby close the opening at the interface between the upper end of the mask and the brow, and thus prevent the ingress of any contaminated fluid therethrough.

In order to hold the mask in place on the wearer's head, it includes the heretofore identified mounting means 31. That mounting means comprises a pair of elongated flexible strips 44 and 46. As can be seen, the front end of the strip 44 is fixedly secured to the mask at one side of the shield 28 contiguous with one end of the frame 30, while the corresponding end 50 of the strip 46 is connected to the mask at the other end of the frame 30. A strip of resilient material, such as rubber, 52 is interconnected between the two remaining ends of the strips 44 and 46 to form a complete band with the mask. This band is arranged to encircle the side and back of the wearer's head as shown in FIG. 1. The resilient strip 52 serves to hold the band tightly in place. The strips 44 and 46 can be made of any suitable material, such as cloth, strong paper, etc.

The material forming the shield 28 is a somewhat flexible plastic material and is at least approximately 10 inches (25.4 cm) high and 7 inches (17.8 cm) wide. With such a construction, the mask serves to cover virtually the entire width of the face, but leaves a sufficient opening on either side of the face to allow proper air circulation to prevent fogging or the build-up of undue heat. The frame and the cushioning strip are approximately ¾ inch (1.9 cm) wide.

Referring to FIGS. 4–6, an alternative and preferred embodiment of a protective mask of this invention is shown generally at 120. This mask comprises a shield means 122 to which an elastic band 124 is secured, for the purpose of permitting the mask to be easily positioned and retained about a user's head.

The shield means 122 is formed of a transparent, imperforate plastics material which is dimensioned to extend substantially over the entire face, in a manner similar to that described earlier in connection with the shield means 28. In fact, the shield means 122 can have the same general height and width dimensions as specified earlier in connection with the shield means 28.

Still referring to FIGS. 4–6, the shield means 122 includes an upper segment 126 which is arcuately shaped from one side edge 128 to the other side edge 128 of said shield means. An anteriorly projecting portion 130 extends downwardly from the upper, arcuately segment 126, and includes an outwardly flaring upper portion 132 and an inwardly flaring lower portion 134. The upper and lower portions 132 and 134 meet a nonsharp curved junction 136, which minimizes visual distortion when the field of view through a section of the mask includes the junction 136.

As stated earlier, shield means 122 can be of the same flexible plastic material as the shield 28, and can be of the same general size as the shield 28 to cover virtually the entire width and height of the faces of virtually all individuals that might possibly wear the mask. Moreover, the shield means 122 perferably is dimensioned to leave a sufficient opening o either side of the face to allow proper air circulation for preventing fogging or the build-up of undue heat.

As can be seen best in FIGS. 4 and 5 the elastic band 124 includes opposed marginal ends 138 which preferably are secured, such as by a suitable adhesive, to the inner surface of the upper arcuate segment 126 of the shield means. A cushioning material 140, which can be the same as the cushioning material 42 employed in the mask 20, is adhered to the inner surface of the upper segment 126 of the shield means 122 to provide a comfortable, conforming fit about the brow of the wearer's head. If desired, a malleable member (not shown), of the same construction as the malleable member 30 in the mask 20, can be provided between the upper segment 126 of the shield means 122 and the cushioning material 140 to permit the upper section of the mask to be formed into close conformity with the wearer's brow.

Form adjusting means 150 are made of a malleable material such as aluminum and are fixedly secured in strips in a longitudinal fashion adjacent each side edge 128 of the shield means 122. Most preferably, the form adjusting means bridge the inwardly flaring lower portion 134 and the outwardly flaring upper portion 132. The form adjusting means 150, because they are malleable, can be bent to better conform the mask to the precise shape of the wearer's facial features and eyegear. In particular, the bending of the form adjusting means foreshortens the shield means 122, causing the sides of such shield means to bow-out, as is schematically shown in phantom representation in FIG. 4, to thereby accommodate the use of varying sizes and shapes of eyewear worn by user's of the mask.

As will be appreciated from the foregoing, the subject invention can provide excellent protection for the whole face against accidental contamination with infected body fluids or other contaminated fluids, while allowing unimpeded and unaltered viewing through the mask, all with a high degree of comfort. Moreover, the mask can be worn along or in combination with other protective means, e.g., conventional masks, hoods, etc., and, in the most preferred embodiment, with a wide variety of eyewear.

Owing to the simple construction of the mask, the mask can be made of low cost, disposable materials, so that it can be readily produced at a low cost.

Without further elaboration, the foregoing will so fully illustrate my invention that others may, by applying current or future knowledge, adopt the same for use under various conditions of service.

I claim:

1. A protective mask for use by a person, said mask comprising mount means for securing said mask onto the head of said person, imperforate shield means supported by said mounting means and disposed therebelow, said shield means being formed of a transparent material and being of a sufficient width and height to cover substantially the entire face of said person, said width being defined between opposed side edges, said shield means including an anteriorly protruding portion, said protruding portion including an outwardly flaring upper portion and a downwardly flaring lower portion, and form adjusting means for adjusting and maintaining the contour of said shield means, said form adjusting means comprising elongate strips of malleable, form-retaining material, each of said strips secured adjacent a different one of said opposed side edges of said shield means and bridging said outwardly flaring upper portion and said downwardly flaring lower portion.

2. The mask of claim wherein said shield means comprises opposed side edges, said form adjusting means comprising elongate strips of malleable, form-retaining material, each of said strips secured adjacent a different one of said opposed side edges of said shield means.

3. The mask of claim 2 wherein said elongate strips of malleable, form-retaining material bridge said outwardly flaring upper portion and said downwardly flaring lower portion.

4. The mask of claim 1 wherein said malleable, form-retaining material comprises aluminum.

5. The mask of claim 1 wherein said anteriorly protruding portion comprises a non-sharp, curved junction between said outwardly flaring upper portion and said downwardly flaring lower portion.

6. The mask of claim 1 wherein said malleable, form-retaining material comprises aluminum.

7. The mask of claim 1 wherein said mounting means comprises a conformable material adapted to be disposed in engagement with the wearer's brow.

8. The mask of claim 7 wherein said conformable material comprises aluminum.

* * * * *